US012802215B2

(12) United States Patent
Yoo et al.

(10) Patent No.: US 12,802,215 B2
(45) Date of Patent: Nov. 17, 2026

(54) GENERATING SYNTHETIC HEALTHY-FOR-AGE BRAIN IMAGES

(71) Applicant: Siemens Healthineers AG, Forchheim (DE)

(72) Inventors: Youngjin Yoo, Princeton, NJ (US); Eli Gibson, Plainsboro, NJ (US); Gengyan Zhao, Plainsboro, NJ (US); Long Xie, Chesterbrook, PA (US); Boris Mailhe, Plainsboro, NJ (US); Dorin Comaniciu, Princeton, NJ (US); Thomas Re, New York, NY (US)

(73) Assignee: Siemens Healthineers AG, Forchheim (DE)

( * ) Notice: Subject to any disclaimer, the term of this patent is extended or adjusted under 35 U.S.C. 154(b) by 300 days.

(21) Appl. No.: 18/628,188

(22) Filed: Apr. 5, 2024

(65) Prior Publication Data

US 2025/0315943 A1 Oct. 9, 2025

(51) Int. Cl.
*G06T 7/00* (2017.01)
*G06T 5/50* (2006.01)
(Continued)

(52) U.S. Cl.
CPC .............. *G06T 7/0012* (2013.01); *G06T 5/50* (2013.01); *G06T 5/70* (2024.01); *G06T 11/00* (2013.01);
(Continued)

(58) Field of Classification Search
CPC ........... G06T 7/0012; G06T 5/50; G06T 5/70; G06T 11/00; G06T 2207/20224;
(Continued)

(56) References Cited

U.S. PATENT DOCUMENTS 11,151,722 B2 * 10/2021 Duchesne ............. G06T 7/0014
2022/0122250 A1 * 4/2022 Besson ................ G06N 3/0464
(Continued)

FOREIGN PATENT DOCUMENTS

WO WO-2024059693 A2 * 3/2024 ............. G16H 50/70

OTHER PUBLICATIONS

Lee et al., "Deep learning-based brain age prediction in normal aging and dementia", Nature Aging, 2022, 46 pgs.
(Continued)

*Primary Examiner* — Matthew C Bella
*Assistant Examiner* — Andrew B. Jones

(57) ABSTRACT

Systems and methods for generating synthetic images representing healthy-for-age images of an anatomical object are provided. 1) one or more input medical images of an anatomical object of a patient and 2) an input age associated with the patient are received. A feature set is extracted from the one or more input medical images. The extracted feature set is encoded with noise based on the input age associated with the patient using a machine learning based noise model. An age associated with the patient is predicted based on the extracted feature set. The encoded feature set is denoised based on the input age associated with the patient and the predicted age associated with the patient using a machine learning based denoising model. One or more synthetic images of the anatomical object of the patient are generated based on the denoised feature set. The one or more synthetic images of the anatomical object of the patient are output.

20 Claims, 7 Drawing Sheets

(51) Int. Cl.

| | |
|---|---|
| ***G06T 5/70*** | (2024.01) |
| ***G06T 11/00*** | (2026.01) |
| ***G06V 10/44*** | (2022.01) |
| ***G06V 40/16*** | (2022.01) |
| ***G16H 30/20*** | (2018.01) |
| ***G16H 30/40*** | (2018.01) |

(52) U.S. Cl.
CPC ............ *G06V 10/44* (2022.01); *G06V 40/178* (2022.01); *G16H 30/20* (2018.01); *G16H 30/40* (2018.01); *G06T 2207/20224* (2013.01); *G06T 2207/30016* (2013.01)

(58) Field of Classification Search
CPC . G06T 2207/30016; G06T 2207/10088; G06T 2207/20081; G06T 2207/20084; G06V 10/44; G06V 40/178; G16H 30/20; G16H 30/40
See application file for complete search history.

(56) References Cited

U.S. PATENT DOCUMENTS

2024/0023878 A1* 1/2024 Tseng ..................... G16H 30/20
2024/0065609 A1* 2/2024 Li ........................ A61B 5/4088

OTHER PUBLICATIONS

Pinaya et al., “Brain imaging generation with latent diffusion models”, arXiv:2209.07162v1, 2022, pp. 1-10.
Wolleb et al., “Diffusion models for medical anomaly detection”, ariv:2203.04306v2, 2022, pp. 1-13.
Sanchez et al., “What is healthy? Generative counterfactual diffusion for lesion localization”, arXiv:2207.12268v1, 2022, pp. 1-11.
Ho et al., “Classifier-free diffusion guidance”, arXiv:2207.12598v1, 2022, pp. 1-14.

* cited by examiner

GENERATING SYNTHETIC HEALTHY-FOR-AGE BRAIN IMAGES

TECHNICAL FIELD

The present invention relates generally to generating synthetic medical images, and in particular to generating synthetic healthy-for-age brain images for pathological aging monitoring and neuro-degenerative abnormality detection.

BACKGROUND

As individuals age, the brain undergoes changes in volume, blood flow, inflammation, etc., resulting in changes in cognitive functions. Modeling the effects of the normal aging process of the brain, and deviations from it, enables the prediction of abnormalities and individual health outcomes and improves understanding of aging related disease. However, conventional modeling of the normal aging process of the brain has seen limited success, particularly at the individual patient level. This is largely due to algorithmic limitations in modeling high anatomical/function variability and the scarcity of adequate imaging data. In particular, it is not possible to directly compare a brain with and without aging-related disease, limiting such conventional modeling of the brain.

BRIEF SUMMARY OF THE INVENTION

In accordance with one or more embodiments, systems and methods for generating synthetic images representing healthy-for-age images of an anatomical object are provided. 1) one or more input medical images of an anatomical object of a patient and 2) an input age associated with the patient are received. A feature set is extracted from the one or more input medical images. The extracted feature set is encoded with noise based on the input age associated with the patient using a machine learning based noise model. An age associated with the patient is predicted based on the extracted feature set. The encoded feature set is denoised based on the input age associated with the patient and the predicted age associated with the patient using a machine learning based denoising model. One or more synthetic images of the anatomical object of the patient are generated based on the denoised feature set. The one or more synthetic images of the anatomical object of the patient are output.

In one embodiment, the encoded feature set is denoised based on a difference between the input age and the predicted age.

In one embodiment, one or more abnormalities in the one or more input medical images are predicted based on the extracted feature set. The one or more synthetic images are generated based on the one or more predicted abnormalities.

In one embodiment, an abnormality map is generated by subtracting the one or more synthetic images from the one or more input medical images. In one embodiment, a quantitative measure of difference in appearance is determined based on the one or more synthetic images and the one or more input medical images. In one embodiment, a predicted age difference is determined as the difference between the input age and the predicted age.

In one embodiment, the machine learning based noise model and the machine learning based denoising model is the same latent diffusion model.

In one embodiment, the one or more synthetic images represent healthy-for-age images of the anatomical object for the input age.

In one embodiment, the anatomical object is a brain of the patient.

These and other advantages of the invention will be apparent to those of ordinary skill in the art by reference to the following detailed description and the accompanying drawings.

DETAILED DESCRIPTION

The present invention generally relates to methods and systems for generating synthetic healthy-for-age brain images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Further, reference herein to pixels of an image may refer equally to voxels of an image and vice versa.

Embodiments described herein provide for a generative diffusion system for generating realistic normative synthetic brain images with age-specific conditioning. The synthetic brain images represent healthy-for-age brain images of a patient. By comparing the synthetic brain images of the patient with real brain images of the patient, deviations between the synthetic brain images and the real brain images can be determined. Such deviations provide for more sensitive biomarkers for improving understanding of aging-related diseases and for predicting individual future health outcomes. Further, such deviations may be used to detect various types of neurological abnormalities, such as, e.g., white matter hyperintensities, brain atrophy, brain tumors, etc. without requiring extensive expert ground truth annotations.

Figure 1:
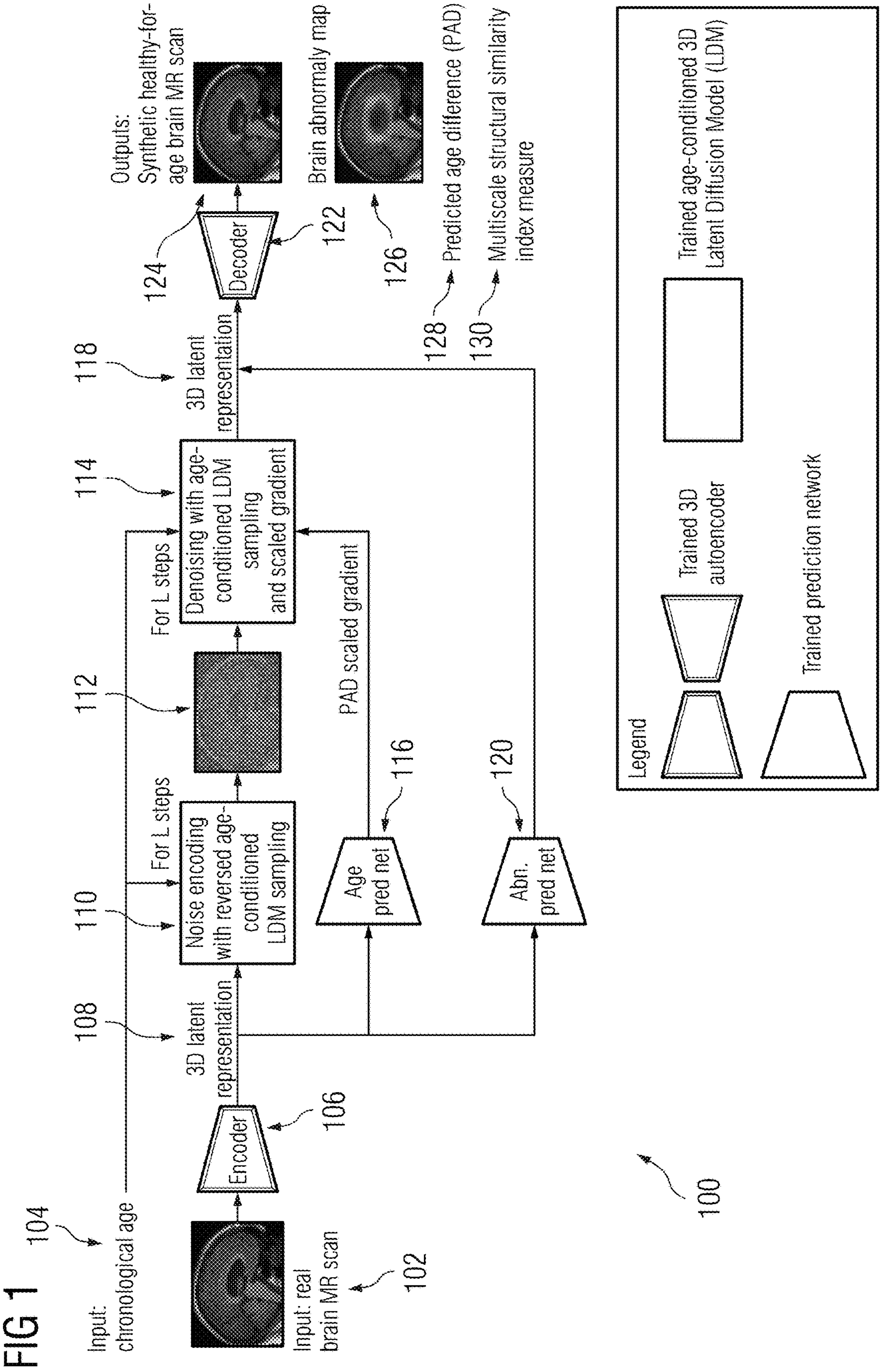
FIG. 1 shows a workflow for generating synthetic medical images of a brain of a patient, in accordance with one or more embodiments.
Figure 2:
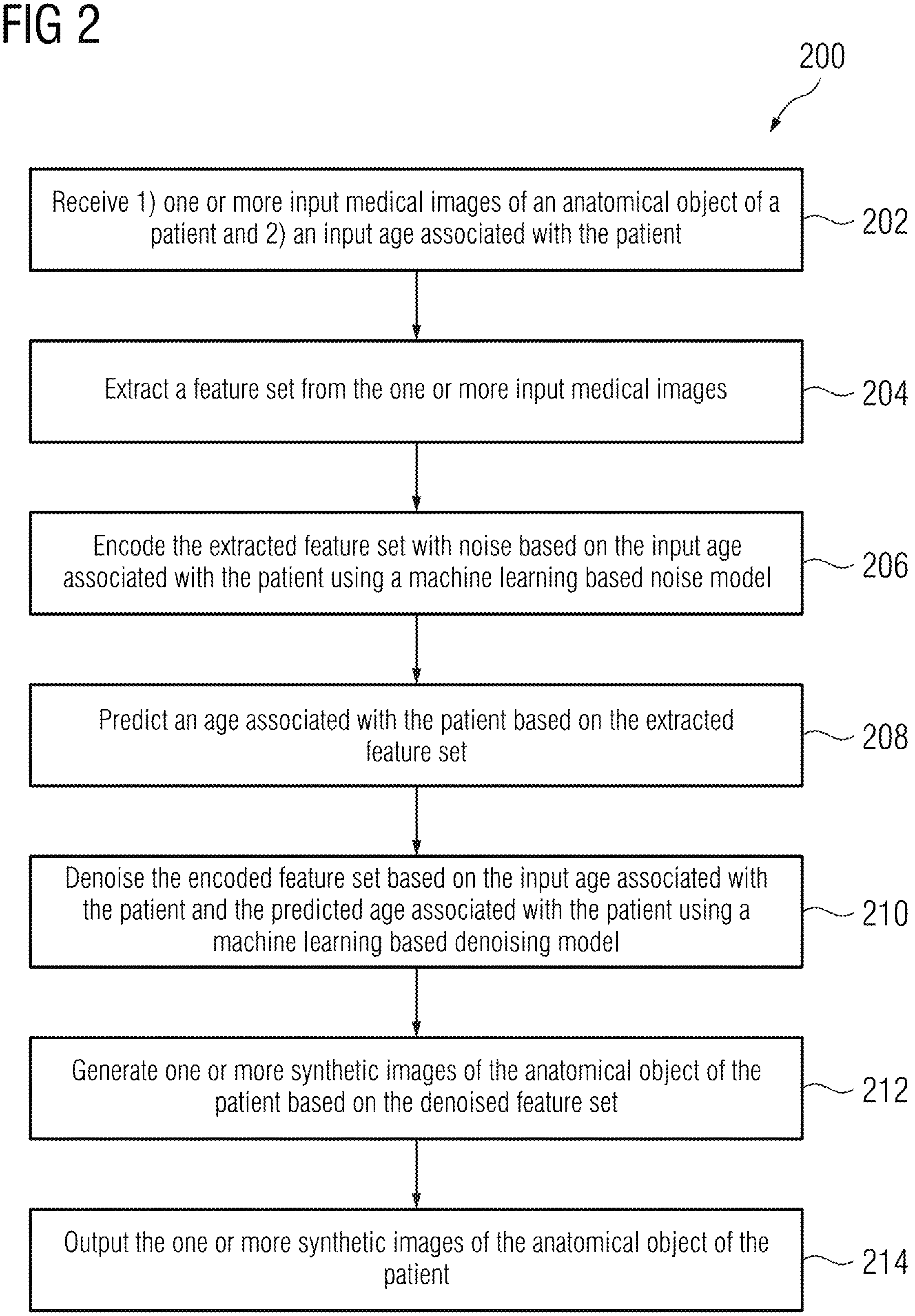
FIG. 2 shows a method for generating synthetic medical images, in accordance with one or more embodiments.

FIG. 1 shows a workflow 100 for generating synthetic medical images of a brain of a patient, in accordance with one or more embodiments. Workflow 100 is performed using trained 3D autoencoders, trained prediction networks, and trained age-conditioned 3D latent diffusion models, as defined in the legend. FIG. 2 shows a method 200 for generating synthetic medical images, in accordance with one or more embodiments. FIG. 1 and FIG. 2 will be described together. The steps of method 200 may be performed by one or more suitable computing devices, such as, e.g., computer 702 of FIG. 7.

At step 202 of FIG. 2, 1) one or more input medical images of an anatomical object of a patient and 2) an input age associated with the patient are received. In one example, as shown in workflow 100 of FIG. 1, the one or more input medical images of the anatomical object is real brain MR (magnetic resonance) scan 102 of the brain of the patient and the input age associated with the patient is chronological age 104.

In one embodiment, the anatomical object of the patient is the brain of the patient. However, the anatomical object may be any other anatomical object of interest of the patient, such as, e.g., other organs, bones, vessels, tumors or other abnormalities, etc. In one embodiment, the one or more input medical images are MRI images. For example, such MRI images may be diffusion tensor imaging, functional MRI, or susceptibility weighted imaging. However, the one or more input medical images may be of any other suitable modality, such as, e.g., CT (computed tomography), US (ultrasound), x-ray, or any other medical imaging modality or combinations of medical imaging modalities. The one or more input medical images may be 2D (two dimensional) images and/or 3D (three dimensional) volumes, and may comprise a single image or a plurality of images.

In one embodiment, the input age associated with the patient is the chronological age of the patient. However, the input age associated with the patient may comprise any other age information associated with the patient (e.g., biological age of the patient). In one embodiment, in addition to the input age associated with the patient, additional conditioning information may be received at step 202 of FIG. 2. Such conditioning information may comprise, for example, an anatomy, sex, or other demographic information associated with the patient.

Figure 7:
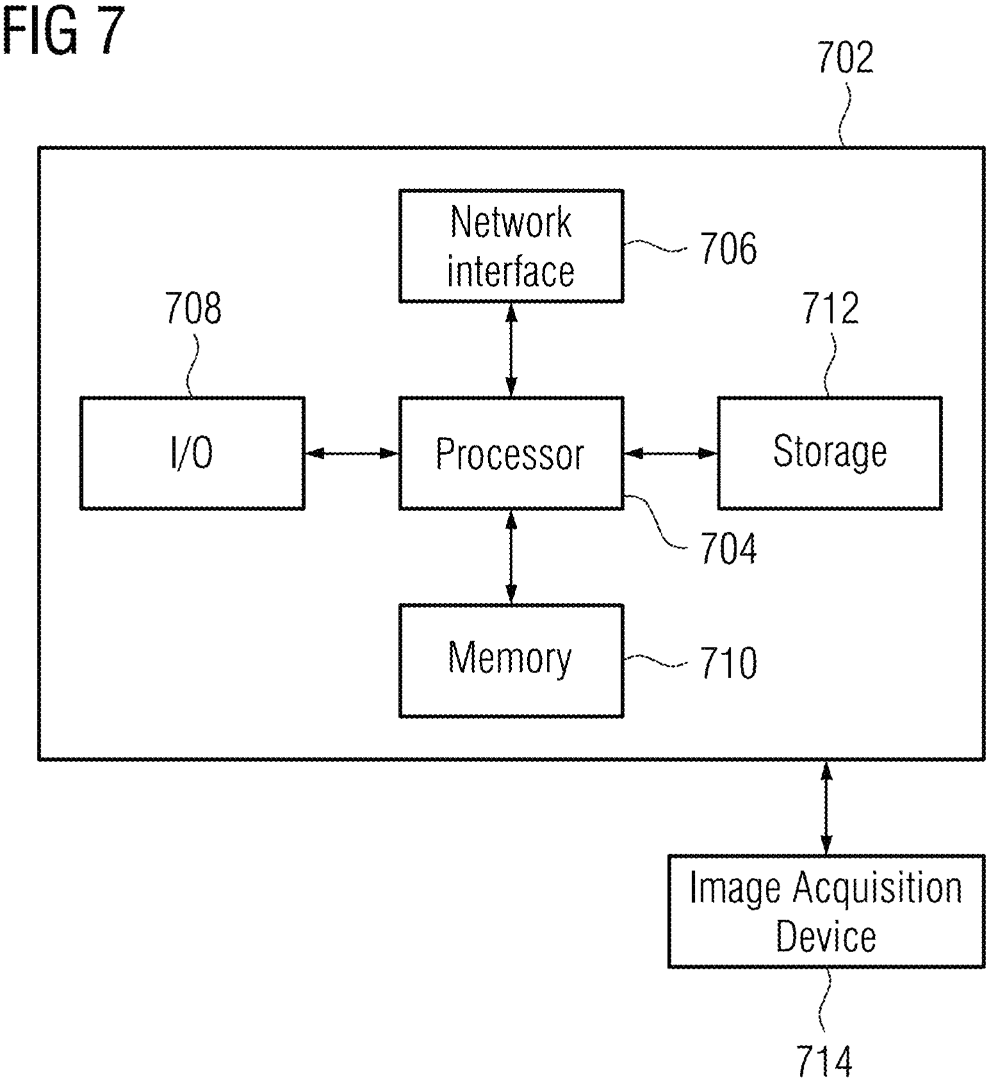
FIG. 7 shows a high-level block diagram of a computer that may be used to implement one or more embodiments.

The one or more input medical images, the input age, and/or the conditioning information may be received, for example, directly from an image acquisition device (e.g., image acquisition device 714 of FIG. 7) as the one or more input medical images are acquired, by loading the one or more input medical images, the input age, and/or the conditioning information from a storage or memory of a computer system (e.g., storage 712 or memory 710 of computer system 702 of FIG. 7), or by receiving the one or more input medical images, the input age, and/or the conditioning information from a remote computer system (e.g., computer system 702 of FIG. 7).

At step 204 of FIG. 2, a feature set is extracted from the one or more input medical images. The feature set may be extracted from the one or more input medical images using a machine learning based encoder network. For example, as shown in workflow 100 of FIG. 1, encoder network 106 encodes real brain MR scan 102 to generate 3D latent representation 108. However, the feature set may be extracted from the one or more input medical images using any other suitable approach.

The encoder network receives as input the one or more input medical images and generates as output the feature set. The feature set represents a lower-dimensional latent representation, which may comprise hidden or underlying attributes of the one or more input medical images that are not directly observable. The latent representation may comprise patterns or relationships between the observed variables in the one or more input medical images. The encoder network may be implemented using any suitable machine learning based model, such as, e.g., an autoencoder.

At step 206 of FIG. 2, the extracted feature set is encoded with noise based on the input age associated with the patient using a machine learning based noise model. For example, as shown in workflow 100 of FIG. 1, extracted feature set 108 is encoded with noise based on chronological age 104 by LDM (latent diffusion model) 110 over L predefined iteration steps to provide an encoded feature set (illustratively represented by noisy image 112).

The noise model receives as input the extracted feature set and the input age associated with the patient (and, in some embodiments, the conditioning information) and generates as output an encoded feature set (encoded with noise). In one embodiment, the noise model is a latent diffusion model. The latent diffusion model starts with a base distribution (e.g., a Gaussian distribution) to serve as the initial state of a generation process. Noise is then iteratively added to the base distribution through a series of diffusion steps. The noise is conditioned on the input age associated with the patient (as well as, in some embodiment, the conditioning information). Each diffusion step involves applying a diffusion process to the current state, gradually transforming it into a more complex distribution. However, the noise model may be any other suitable machine learning based model for encoding the extracted feature set with noise.

At step 208 of FIG. 2, an age associated with the patient is predicted based on the extracted feature set. The age associated with the patient may be predicted using any suitable machine learning based age prediction network. The age prediction network receives as input the extracted feature set (extracted from the one or more input medical images at step 204 of FIG. 2) and generates as output a predicted age of the patient. In one example, as shown in workflow 100 of FIG. 1, age prediction network 116 predicts an age associated with the patient based on 3D latent representation 108.

At step 210 of FIG. 2, the encoded feature set is denoised based on the input age associated with the patient and the predicted age associated with the patient using a machine learning based denoising model. For example, as shown in workflow 100 of FIG. 1, the extracted feature set (illustratively represented by noisy image 112) is denoised based on chronological age 104 and the predicted age (predicted by age prediction network 116) by LDM 114 over L predefined iteration steps to generate 3D latent representation 118.

The denoising model receives as input the encoded feature set (encoded with noise at step 206 of FIG. 2), the input age associated with the patient (and, in some embodiments, the conditioning information), and the predicted age associated with the patient and generates as output a denoised feature set. In one embodiment, the denoising model is a latent diffusion model. Similar to adding noise (at step 206 of FIG. 2), the latent diffusion model starts with a base distribution (e.g., a Gaussian distribution) to serve as the initial state. However, instead of adding noise as in the generative case, the diffusion process iteratively diffuses the noise away from the encoded feature set towards the base distribution. The denoising is conditioned on the input age associated with the patient (as well as, in some embodiment, the conditioning information) and the predicted age associated with the patient. In one embodiment, the denoising is performed with a PAD (predicted age difference) scaled gradient. The predicted age difference is determined as the difference between the input age associated with the patient and the predicted age associated with the patient. The gradient determines how aggressively the latent diffusion model adjusts the latent space to remove noise from the encoded feature set. Accordingly, a relatively larger predicted age difference will result in a larger PAD scaled gradient, which will provide stronger adjustments to the latent representation of the encoded feature set and lead to more denoising. Conversely, a relatively smaller predicted age difference will result in a smaller PAD scaled gradient, which will provide weaker adjustments to the latent representation of the encoded feature set and lead to less denoising. In one embodiment, for example where the predicted age of the patient is not available, the gradient scaling could be performed by implicit guidance with attention mechanism along with age conditioning. However, the denoising model may be any other suitable machine learning based model for denoising the encoded feature set.

In one embodiment, the latent diffusion model for denoising the encoded feature set at step 210 and the latent diffusion model for encoding the extracted feature set with noise at step 206 are the same latent diffusion model. In this embodiment, the latent diffusion model is configured with different formulations for adding noise and removing noise. In other embodiment, the latent diffusion model for denoising the encoded feature set at step 210 and the latent diffusion model for encoding the extracted feature set with noise at step 206 are different latent diffusion models.

At step 212 of FIG. 2, one or more synthetic images of the anatomical object of the patient is generated based on the denoised feature set. The one or more synthetic images of the anatomical object of the patient may be generated using a machine learning based decoder network. For example, as shown in workflow 100 of FIG. 1, decoder network 122 decodes 3D latent representation 118 to generate synthetic healthy-for-age brain MR scan 124.

The decoder network receives as input the denoised feature set and generates as output the one or more synthetic images of the anatomical object of the patient. The decoder network may be implemented using any suitable machine learning based model, such as, e.g., an autoencoder. The one or more synthetic images of the anatomical object of the patient represent healthy-for-age images of the anatomical object for the input age associated with the patient.

Optionally, in one embodiment, the one or more synthetic images of the anatomical object of the patient is further generated based on predicted abnormalities detected in the one or more input medical images using an abnormality prediction network. The abnormality prediction network receives as input the extracted feature set (extracted from the one or more input medical images at step 204 of FIG. 2) and generates as output one or more predicted abnormalities. The decoder network further receives as input the predicted abnormalities and generates as output the one or more synthetic images of the anatomical object of the patient. For example, as shown in workflow 100 of FIG. 1, abnormality prediction network 120 predicts abnormalities from 3D latent representation 108 and decoder network 122 generates the synthetic healthy-for-age brain MR scan 124 based on the predicted abnormalities.

At step 214 of FIG. 2, the one or more synthetic images of the anatomical object of the patient is output. For example, the one or more synthetic images can be output by displaying the one or more synthetic images on a display device of a computer system (e.g., I/O 708 of computer 702 of FIG. 7), storing the one or more synthetic images on a storage or memory of a computer system (e.g., storage 712 or memory 710 of computer system 702 of FIG. 7), or by transmitting the one or more synthetic images to a remote computer system (e.g., computer system 702 of FIG. 7).

In one embodiment, an abnormality map may be generated by analyzing the difference in appearance between the one or more synthetic images of the anatomical object of the patient (representing healthy-for-age images of the anatomical object) and the one or more input medical images of the anatomical object of the patient (representing real images of the anatomical object). For example, in workflow 100 of FIG. 1, the brain abnormality map may be brain abnormality map 126. The abnormality map may be generated by subtracting the one or more synthetic images of the anatomical object of the patient from the one or more input medical images of the anatomical object of the patient.

In one embodiment, a quantitative measure of difference in appearance between the one or more synthetic images of the anatomical object of the patient and the one or more input medical images of the anatomical object of the patient is determined. In one example, the quantitative measure may be normalized mutual information or MS-SSIM (multiscale structural similarity index measure). For example, in workflow 100 of FIG. 1, the quantitative measure may be multiscale structural similarity index measure 130. Normalized mutual information is a metric that can represents brain structural shape difference between two brain images. SSIM quantifies perceived differences in structural information between two images, which provides higher-level image difference information than voxel-based metrics such as, e.g., mean-square-error or peak signal-to-noise ratio. MS-SSIM is conducted over multiple scales through several sub-sampling processes, which can measure both global and local structural changes in brain shape occurred by an underlying pathology.

In one embodiment, a predicted age difference is determined as the difference between the input age of the patient and the predicted age of the patient is determined. For example, in workflow 100 of FIG. 1, the predicted age difference may be PAD (predicted age difference) 128. The predicted age difference may provide prognostic value to better distinguish from pathological aging.

In one embodiment, an uncertainty estimate of the abnormality map and/or quantitative measure may be provided by ensembling if a probabilistic diffusion sampler is used. If a probabilistic diffusion sample is used, multiple synthetic healthy-for-age images can be generated. Each healthy image sample can create an abnormality map. By computing variance between the multiple abnormality map samples, one can estimate the uncertainty of the abnormality map.

In one embodiment, the one or more synthetic images are used for measuring brain appearance deviations in white matter hyperintensity volume/count, brain atrophy, and shape change metrics (e.g., MS-SSIM) from the one or more input medical images to detect and quantify abnormal neurological aging as well as other disease progression.

In one embodiment, embodiments described herein may be used for longitudinal monitoring. Where one or more previously acquired images is provided as the one or more input medical images, the one or more synthetic images can be compared to the one or more previously acquired images to estimate the aging progression in a longitudinal manner.

In one embodiment, for more accurate generative modeling of non-pathological brain aging, the conditioning mechanism of the noise model and denoising model can be performed not only with the input age but also with biochemical deficits, such as, e.g., oxidative damage, mitochondrial impairment, changes in glucose-energy metabolism, and neuroinflammation.

The encoder network (e.g., encoder network 106 of FIG. 1 or the encoder network utilized at step 204 of FIG. 2), the noise model (e.g., LDM 110 of FIG. 1 or the noise model utilized at step 206 of FIG. 2), the denoising model (e.g., LDM 114 of FIG. 1 or the denoising model utilized at step 210 of FIG. 2), the decoder network (e.g., decoder network 122 of FIG. 1 or the decoder network utilized at step 212 of FIG. 2), the age prediction model (e.g., age prediction network 116 of FIG. 1 or the age prediction network utilized at step 208 of FIG. 2), and the abnormality prediction model (e.g., abnormality prediction network 120 of FIG. 1 or the abnormality prediction network utilized at step 212 of FIG. 2) are trained during a prior offline or training stage. The training is performed using healthy and abnormal training images of the anatomical object of patients, along with the ages of the patients. The encoder network is first trained to encode the training images into feature sets representing lower-dimensional latent representations using, e.g., a combination of L1 loss, perceptual loss, a patch-based adversarial object, and KL (Kullback-Leibler) regularization. Then, a latent diffusion model is trained (as the noise model and the denoising model) with the ages of the patients conditioning the feature set compressed by the machine learning based encoder network. The age prediction network is trained with the training images (or the feature set extracted therefrom by the encoder network) and their corresponding ages of the patients. A prediction network trained with another dataset or a publicly available pre-trained network can also be used for the age prediction task. The abnormality prediction network is trained with the training images (or the feature set extracted therefrom by the machine learning based encoder network) and their corresponding ground truth abnormalities.

Embodiments described herein are described with respect to the claimed systems as well as with respect to the claimed methods. Features, advantages or alternative embodiments herein can be assigned to the other claimed objects and vice versa. In other words, claims and embodiments for the systems can be improved with features described or claimed in the context of the respective methods. In this case, the functional features of the method are implemented by physical units of the system.

Furthermore, certain embodiments described herein are described with respect to methods and systems utilizing trained machine learning models, as well as with respect to methods and systems for providing trained machine learning models. Features, advantages or alternative embodiments herein can be assigned to the other claimed objects and vice versa. In other words, claims and embodiments for providing trained machine learning models can be improved with features described or claimed in the context of utilizing trained machine learning models, and vice versa. In particular, datasets used in the methods and systems for utilizing trained machine learning models can have the same properties and features as the corresponding datasets used in the methods and systems for providing trained machine learning models, and the trained machine learning models provided by the respective methods and systems can be used in the methods and systems for utilizing the trained machine learning models.

In general, a trained machine learning model mimics cognitive functions that humans associate with other human minds. In particular, by training based on training data the machine learning model is able to adapt to new circumstances and to detect and extrapolate patterns. Another term for "trained machine learning model" is "trained function."

In general, parameters of a machine learning model can be adapted by means of training. In particular, supervised training, semi-supervised training, unsupervised training, reinforcement learning and/or active learning can be used. Furthermore, representation learning (an alternative term is "feature learning") can be used. In particular, the parameters of the machine learning models can be adapted iteratively by several steps of training. In particular, within the training a certain cost function can be minimized. In particular, within the training of a neural network the backpropagation algorithm can be used.

In particular, the machine learning models disclosed herein, such as, e.g., encoder network 106, LDM 110, LDM 114, decoder network 122, age prediction network 116, or abnormality prediction network 120 of FIG. 1 or the encoder network utilized at step 204, the noise model utilized at step 206, the denoising model utilized at step 210, the decoder network utilized at step 212, the age prediction network utilized at step 208, or the abnormality prediction network utilized at step 212 of FIG. 2, can comprise, for example, a neural network, a support vector machine, a decision tree and/or a Bayesian network, and/or the machine learning model can be based on, for example, k-means clustering, Q-learning, genetic algorithms and/or association rules. In particular, a neural network can be, e.g., a deep neural network, a convolutional neural network or a convolutional deep neural network. Furthermore, a neural network can be, e.g., an adversarial network, a deep adversarial network and/or a generative adversarial network.

Figure 3:
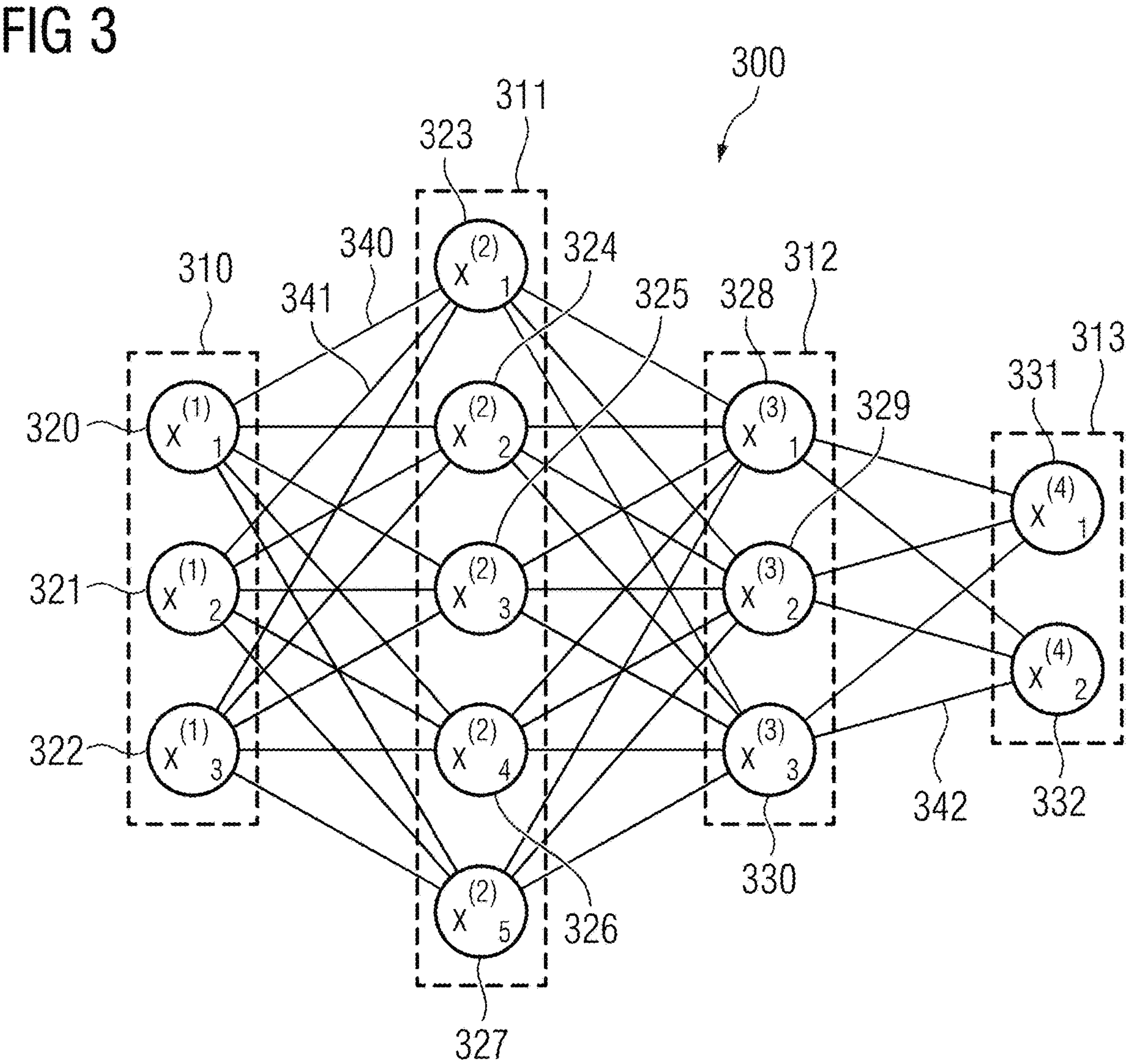
FIG. 3 shows an exemplary artificial neural network that may be used to implement one or more embodiments.

FIG. 3 shows an embodiment of an artificial neural network 300 that may be used to implement one or more machine learning models described herein. Alternative terms for "artificial neural network" are "neural network", "artificial neural net" or "neural net".

The artificial neural network 300 comprises nodes 320, . . . , 332 and edges 340, . . . , 342, wherein each edge 340, . . . , 342 is a directed connection from a first node 320, . . . , 332 to a second node 320, . . . , 332. In general, the first node 320, . . . , 332 and the second node 320, . . . 332 are different nodes 320, . . . , 332, it is also possible that the first node 320, . . . , 332 and the second node 320, . . . , 332 are identical. For example, in FIG. 3 the edge 340 is a directed connection from the node 320 to the node 323, and the edge 342 is a directed connection from the node 330 to the node 332. An edge 340, . . . , 342 from a first node 320, . . . , 332 to a second node 320, . . . , 332 is also denoted as "ingoing edge" for the second node 320, . . . , 332 and as "outgoing edge" for the first node 320, . . . , 332.

In this embodiment, the nodes 320, . . . , 332 of the artificial neural network 300 can be arranged in layers 310, . . . , 313, wherein the layers can comprise an intrinsic order introduced by the edges 340, . . . , 342 between the nodes 320, . . . , 332. In particular, edges 340, . . . , 342 can exist only between neighboring layers of nodes. In the displayed embodiment, there is an input layer 310 comprising only nodes 320, . . . , 322 without an incoming edge, an output layer 313 comprising only nodes 331, 332 without outgoing edges, and hidden layers 311, 312 in-between the input layer 310 and the output layer 313. In general, the number of hidden layers 311, 312 can be chosen arbitrarily. The number of nodes 320, . . . , 322 within the input layer 310 usually relates to the number of input values of the neural network, and the number of nodes 331, 332 within the output layer 313 usually relates to the number of output values of the neural network.

In particular, a (real) number can be assigned as a value to every node 320, . . . , 332 of the neural network 300. Here, $x^{(n)}_i$ denotes the value of the i-th node 320, . . . , 332 of the n-th layer 310, . . . , 313. The values of the nodes 320, . . . , 322 of the input layer 310 are equivalent to the input values of the neural network 300, the values of the nodes 331, 332 of the output layer 313 are equivalent to the output value of the neural network 300. Furthermore, each edge 340, . . . , 342 can comprise a weight being a real number, in particular, the weight is a real number within the interval [−1, 1] or within the interval [0, 1]. Here, $w^{(m,n)}_{i,j}$ denotes the weight of the edge between the i-th node 320, . . . , 332 of the m-th layer 310, . . . , 313 and the j-th node 320, . . . , 332 of the n-th layer 310, . . . , 313. Furthermore, the abbreviation $w^{(n)}_{i,j}$ is defined for the weight $w^{(n,n+1)}_{i,j}$.

In particular, to calculate the output values of the neural network 300, the input values are propagated through the neural network. In particular, the values of the nodes 320, . . . , 332 of the (n+1)-th layer 310, . . . , 313 can be calculated based on the values of the nodes 320, . . . , 332 of the n-th layer 310, . . . , 313 by $$x^{(n+1)}{}_j = f\left(\sum_i x^{(n)}{}_i \cdot w^{(n)}{}_{i,j}\right).$$

Herein, the function f is a transfer function (another term is "activation function"). Known transfer functions are step functions, sigmoid function (e.g., the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 310 are given by the input of the neural network 300, wherein values of the first hid-den layer 311 can be calculated based on the values of the input layer 310 of the neural network, wherein values of the second hidden layer 312 can be calculated based in the values of the first hidden layer 311, etc.

In order to set the values $w^{(m,n)}_{i,j}$ for the edges, the neural network 300 has to be trained using training data. In particular, training data comprises training input data and training output data (denoted as $t_i$). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w'^{(n)}{}_{i,j} = w^{(n)}{}_{i,j} - \gamma \cdot \delta^{(n)}{}_j \cdot x^{(n)}{}_i$$

wherein $\gamma$ is a learning rate, and the numbers $\delta^{(n)}_j$ can be recursively calculated as $$\delta^{(n)}{}_j = \left(\sum_k \delta^{(n+1)}{}_k \cdot w^{(n+1)}{}_{j,k}\right) \cdot f'\left(\sum_i x^{(n)}{}_i \cdot w^{(n)}{}_{i,j}\right)$$

based on $\delta^{(n+1)}_{j,\ if\ the\ (n+}$1)-th layer is not the output layer, and $$\delta^{(n)}{}_j = \left(x^{(n+1)}{}_j - t^{(n+1)}{}_j\right) \cdot f'\left(x^{(n)}{}_i \cdot w^{(n)}{}_{i,j}\right)$$

if the (n+1)-th layer is the output layer 313, wherein f' is the first derivative of the activation function, and $t^{(n+1)}_j$ is the comparison training value for the j-th node of the output layer 313.

A convolutional neural network is a neural network that uses a convolution operation instead general matrix multiplication in at least one of its layers (so-called "convolutional layer"). In particular, a convolutional layer performs a dot product of one or more convolution kernels with the convolutional layer's input data/image, wherein the entries of the one or more convolution kernel are the parameters or weights that are adapted by training. In particular, one can use the Frobenius inner product and the ReLU activation function. A convolutional neural network can comprise additional layers, e.g., pooling layers, fully connected layers, and normalization layers.

By using convolutional neural networks input images can be processed in a very efficient way, because a convolution operation based on different kernels can extract various image features, so that by adapting the weights of the convolution kernel the relevant image features can be found during training. Furthermore, based on the weight-sharing in the convolutional kernels less parameters need to be trained, which prevents overfitting in the training phase and allows to have faster training or more layers in the network, improving the performance of the network.

Figure 4:
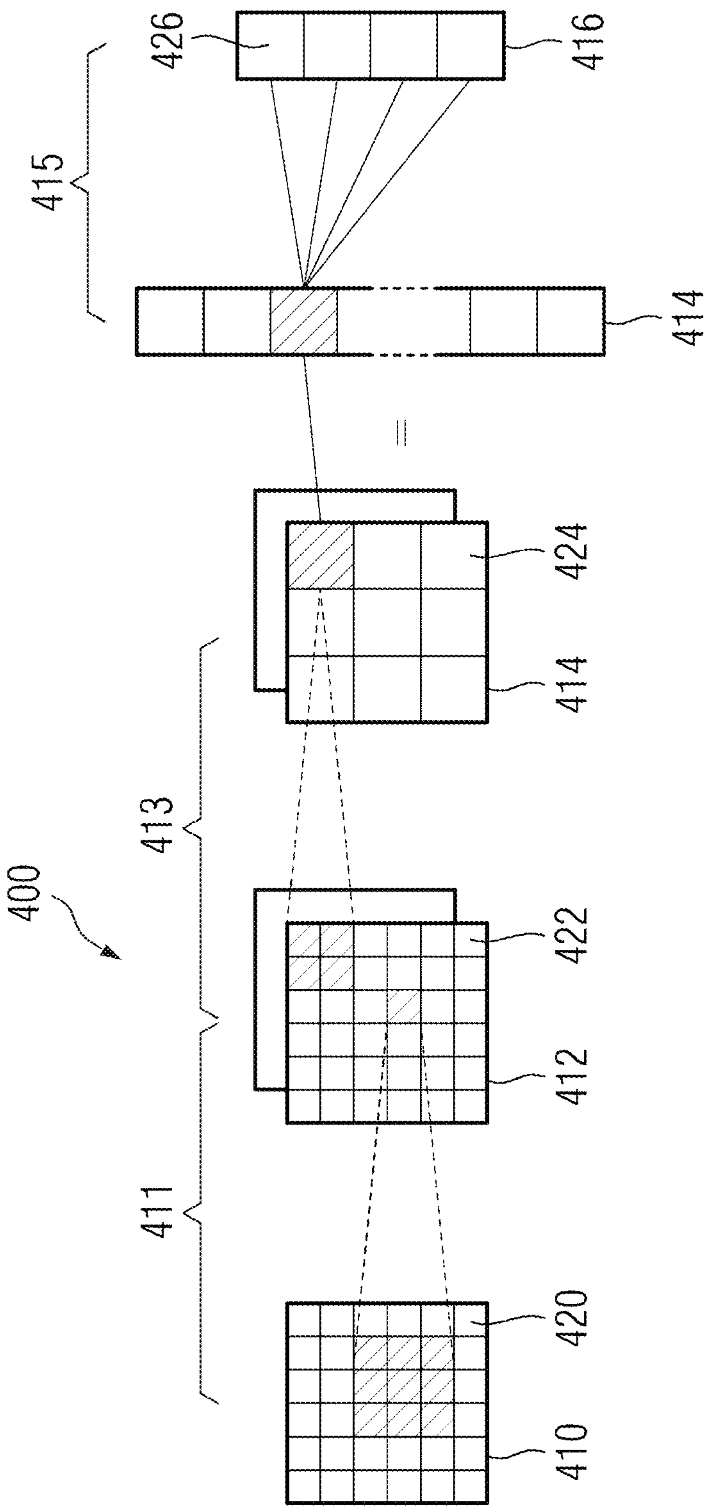
FIG. 4 shows a convolutional neural network that may be used to implement one or more embodiments.

FIG. 4 shows an embodiment of a convolutional neural network 400 that may be used to implement one or more machine learning models described herein. In the displayed embodiment, the convolutional neural network comprises 400 an input node layer 410, a convolutional layer 411, a pooling layer 413, a fully connected layer 414 and an output node layer 416, as well as hidden node layers 412, 414. Alternatively, the convolutional neural network 400 can comprise several convolutional layers 411, several pooling layers 413 and several fully connected layers 415, as well as other types of layers. The order of the layers can be chosen arbitrarily, usually fully connected layers 415 are used as the last layers before the output layer 416.

In particular, within a convolutional neural network 400 nodes 420, 422, 424 of a node layer 410, 412, 414 can be considered to be arranged as a d-dimensional matrix or as a d-dimensional image. In particular, in the two-dimensional case the value of the node 420, 422, 424 indexed with i and j in the n-th node layer 410, 412, 414 can be denoted as x(n)[i, j]. However, the arrangement of the nodes 420, 422, 424 of one node layer 410, 412, 414 does not have an effect on the calculations executed within the convolutional neural network 400 as such, since these are given solely by the structure and the weights of the edges.

A convolutional layer 411 is a connection layer between an anterior node layer 410 (with node values x(n−1)) and a posterior node layer 412 (with node values x(n)). In particular, a convolutional layer 411 is characterized by the structure and the weights of the incoming edges forming a convolution operation based on a certain number of kernels. In particular, the structure and the weights of the edges of the convolutional layer 411 are chosen such that the values x(n) of the nodes 422 of the posterior node layer 412 are calculated as a convolution x(n)=K*x(n−1) based on the values x(n−1) of the nodes 420 anterior node layer 410, where the convolution * is defined in the two-dimensional case as $$x_k^{(n)}[i, j] = (K * x^{(n-1)})[i, j] = \sum_{i'} \sum_{j'} K[i', j'] \cdot x^{(n-1)}[i - i', j - j'].$$

Here the kernel K is a d-dimensional matrix (in this embodiment, a two-dimensional matrix), which is usually small compared to the number of nodes 420, 422 (e.g., a 3×3 matrix, or a 5×5 matrix). In particular, this implies that the weights of the edges in the convolution layer 411 are not independent, but chosen such that they produce said convolution equation. In particular, for a kernel being a 3×3 matrix, there are only 9 independent weights (each entry of the kernel matrix corresponding to one independent weight), irrespectively of the number of nodes 420, 422 in the anterior node layer 410 and the posterior node layer 412.

In general, convolutional neural networks 400 use node layers 410, 412, 414 with a plurality of channels, in particular, due to the use of a plurality of kernels in convolutional layers 411. In those cases, the node layers can be considered as (d+1)-dimensional matrices (the first dimension indexing the channels). The action of a convolutional layer 411 is then a two-dimensional example defined as $$x^{(n)}{}_b[i, j] = \sum_a K_{a,b} * x^{(n-1)}{}_a[i, j] = \sum_a \sum_{i'} \sum_{j'} K_{a,b}[i', j'] \cdot x^{(n-1)}{}_a[i - i', j - j']$$

where $x^{(n-1)}{}_a$ corresponds to the a-th channel of the anterior node layer 410, $x^{(n)}{}_b$ corresponds to the b-th channel of the posterior node layer 412 and $K_{a,b}$ corresponds to one of the kernels. If a convolutional layer 411 acts on an anterior node layer 410 with A channels and outputs a posterior node layer 412 with B channels, there are A·B independent d-dimensional kernels $K_{a,b}$.

In general, in convolutional neural networks 400 activation functions are used. In this embodiment re ReLU (acronym for "Rectified Linear Units") is used, with R(z)=max(0, z), so that the action of the convolutional layer 411 in the two-dimensional example is $$x^{(n)}{}_b[i, j] = R\left(\sum_a K_{a,b} * x^{(n-1)}{}_a[i, j]\right) = R\left(\sum_a \sum_{i'} \sum_{j'} K_{a,b}[i', j'] \cdot x^{(n-1)}{}_a[i - i', j - j']\right)$$

It is also possible to use other activation functions, e.g., ELU (acronym for "Exponential Linear Unit"), LeakyReLU, Sigmoid, Tanh or Softmax.

In the displayed embodiment, the input layer 410 comprises 36 nodes 420, arranged as a two-dimensional 6×6 matrix. The first hidden node layer 412 comprises 72 nodes 422, arranged as two two-dimensional 6×6 matrices, each of the two matrices being the result of a convolution of the values of the input layer with a 3×3 kernel within the convolutional layer 411. Equivalently, the nodes 422 of the first hidden node layer 412 can be interpreted as arranged as a three-dimensional 2×6×6 matrix, wherein the first dimension correspond to the channel dimension.

The advantage of using convolutional layers 411 is that spatially local correlation of the input data can exploited by enforcing a local connectivity pattern between nodes of adjacent layers, in particular by each node being connected to only a small region of the nodes of the preceding layer.

A pooling layer 413 is a connection layer between an anterior node layer 412 (with node values x(n−1)) and a posterior node layer 414 (with node values x(n)). In particular, a pooling layer 413 can be characterized by the structure and the weights of the edges and the activation function forming a pooling operation based on a non-linear pooling function f. For example, in the two-dimensional case the values x(n) of the nodes 424 of the posterior node layer 414 can be calculated based on the values x(n−1) of the nodes 422 of the anterior node layer 412 as $$x^{(n)}{}_b[i, j] = f\left(x^{(n-1)}[id_1, jd_2], \ldots , x^{(n-1)}{}_b[(i+1)d_1 - 1, (j+1)d_2 - 1]\right)$$

In other words, by using a pooling layer 413 the number of nodes 422, 424 can be reduced, by re-placing a number d1·d2 of neighboring nodes 422 in the anterior node layer 412 with a single node 422 in the posterior node layer 414 being calculated as a function of the values of said number of neighboring nodes. In particular, the pooling function f can be the max-function, the average or the L2-Norm. In particular, for a pooling layer 413 the weights of the incoming edges are fixed and are not modified by training.

The advantage of using a pooling layer 413 is that the number of nodes 422, 424 and the number of parameters is reduced. This leads to the amount of computation in the network being reduced and to a control of overfitting.

In the displayed embodiment, the pooling layer 413 is a max-pooling layer, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

In general, the last layers of a convolutional neural network 400 are fully connected layers 415. A fully connected layer 415 is a connection layer between an anterior node layer 414 and a posterior node layer 416. A fully connected layer 413 can be characterized by the fact that a majority, in particular, all edges between nodes 414 of the anterior node layer 414 and the nodes 416 of the posterior node layer are present, and wherein the weight of each of these edges can be adjusted individually.

In this embodiment, the nodes 424 of the anterior node layer 414 of the fully connected layer 415 are displayed both as two-dimensional matrices, and additionally as non-related nodes (indicated as a line of nodes, wherein the number of nodes was reduced for a better presentability). This operation is also denoted as "flattening". In this embodiment, the number of nodes 426 in the posterior node layer 416 of the fully connected layer 415 smaller than the number of nodes 424 in the anterior node layer 414. Alternatively, the number of nodes 426 can be equal or larger.

Furthermore, in this embodiment the Softmax activation function is used within the fully connected layer 415. By applying the Softmax function, the sum the values of all nodes 426 of the output layer 416 is 1, and all values of all nodes 426 of the output layer 416 are real numbers between 0 and 1. In particular, if using the convolutional neural network 400 for categorizing input data, the values of the output layer 416 can be interpreted as the probability of the input data falling into one of the different categories.

In particular, convolutional neural networks 400 can be trained based on the backpropagation algorithm. For preventing overfitting, methods of regularization can be used, e.g., dropout of nodes 420, . . . , 424, stochastic pooling, use of artificial data, weight decay based on the L1 or the L2 norm, or max norm constraints.

According to an aspect, the machine learning model may comprise one or more residual networks (ResNet). In particular, a ResNet is an artificial neural network comprising at least one jump or skip connection used to jump over at least one layer of the artificial neural network. In particular, a ResNet may be a convolutional neural network comprising one or more skip connections respectively skipping one or more convolutional layers. According to some examples, the ResNets may be represented as m-layer ResNets, where m is the number of layers in the corresponding architecture and, according to some examples, may take values of 34, 50, 101, or 152. According to some examples, such an m-layer ResNet may respectively comprise $(m-2)/2$ skip connections.

A skip connection may be seen as a bypass which directly feeds the output of one preceding layer over one or more bypassed layers to a layer succeeding the one or more bypassed layers. Instead of having to directly fit a desired mapping, the bypassed layers would then have to fit a residual mapping "balancing" the directly fed output.

Fitting the residual mapping is computationally easier to optimize than the directed mapping. What is more, this alleviates the problem of vanishing/exploding gradients during optimization upon training the machine learning models: if a bypassed layer runs into such problems, its contribution may be skipped by regularization of the directly fed output. Using ResNets thus brings about the advantage that much deeper networks may be trained.

A generative adversarial model (an acronym is GA model) comprises a generative function and a discriminative function, wherein the generative function creates synthetic data, and the discriminative function distinguishes between synthetic and real data. By training the generative function and/or the discriminative function on the one hand the generative function is configured to create synthetic data which is incorrectly classified by the discriminative function as real, on the other hand the discriminative function is configured to distinguish between real data and synthetic data generated by the generative function. In the notion of game theory, a generative adversarial model can be interpreted as a zero-sum game. The training of the generative function and/or of the discriminative function is based, in particular, on the minimization of a cost function.

By using a GA model, based on a set of training data synthetic data can be generated that has the same characteristics as the training data set. The training of the GA model can be based on data not being annotated (unsupervised learning), so that there is low effort in training a GA model.

Figure 5:
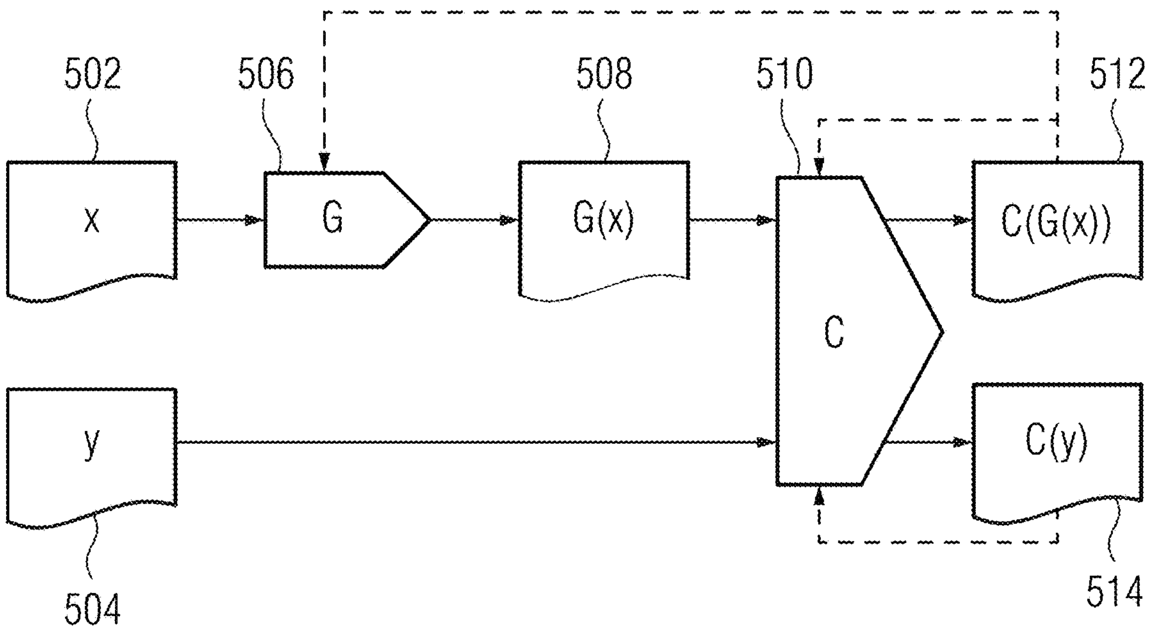
FIG. 5 shows a data flow diagram using a generating adversarial network that may be used to implement one or more embodiments.

FIG. 5 shows a data flow diagram according to an embodiment for using a generative adversarial network for creating synthetic output data G(x) 508 based on input data x 502 that is indistinguishable from real output data y 504, in accordance with one or more embodiments. The synthetic output data G(x) 508 has the same structure as the real output data y 504, but its content is not derived from real world data.

The generative adversarial network comprises a generator function G 506 and a classifier function C 510 which are trained jointly. The task of the generator function G 506 is to provide realistic synthetic output data G(x) 508 based on input data x 502, and the task of the classifier function C 510 is to distinguish between real output data y 504 and synthetic output data G(x) 508. In particular, the output of the classifier function C 510 is a real number between 0 and 1 corresponding to the probability of the input value being real data, so that an ideal classifier function would calculate an output value of C(y) 514≈1 for real data y 504 and C(G(x)) 512≈0 for synthetic data G(x) 508.

Within the training process, parameters of the generator function G 506 are adapted so that the synthetic output data G(x) 508 has the same characteristics as real output data y 504, so that the classifier function C 510 cannot distinguish between real and synthetic data anymore. At the same time, parameters of the classifier function C 510 are adapted so that it distinguishes between real and synthetic data in the best possible way. Here, the training relies on pairs comprising input data x 502 and the corresponding real output data y 504. Within a single training step, the generator function G 506 is applied to the input data x 502 for generating synthetic output data G(x) 508. Furthermore, the classifier function C 510 is applied to the real output data y 504 for generating a first classification result C(y) 514. Additionally, the classifier function C 510 is applied to the synthetic output data G(x) 508 for generating a second classification result C(G(x)) 512.

Adapting the parameters of the generative function G 506 and the classifier function C 510 is based on minimizing a cost function by using the backpropagation algorithm, respectively. In this embodiment, the cost function $K_C$ for the classifier function C 510 is $K_C \propto -\mathrm{BCE}(C(y), 1) - \mathrm{BCE}(C(G(x), 0)$, wherein BCE denotes the binary cross entropy defined as $\mathrm{BCE}(z, z') = z' \cdot \log(z) + (1-z') \cdot \log(1-z)$. By using this cost function, both wrongly classifying real output data as synthetic (indicated by $C(y)=0$) and wrongly classifying synthetic output data as real (indicated as C(G(x)) 512≈1) increases the cost function $K_C$ to be minimized. Furthermore, the cost function $K_G$ for the generator function G 506 is $K_G \propto -\mathrm{BCE}(C(G(x), 1) = -\log(C(G(x))$. By using this cost function, correctly classified synthetic output data (indicated as C(G(x)) 512≈0) leads to an increase of the cost function $K_G$ to be minimized.

In particular, a recurrent machine learning model is a machine learning model whose output does not only depend on the input value and the parameters of the machine learning model adapted by the training process, but also on a hidden state vector, wherein the hidden state vector is based on previous inputs used on for the recurrent machine learning model. In particular, the recurrent machine learning model can comprise additional storage states or additional structures that incorporate time delays or comprise feedback loops.

In particular, the underlying structure of a recurrent machine learning model can be a neural network, which can be denoted as recurrent neural network. Such a recurrent neural network can be described as an artificial neural network where connections between nodes form a directed graph along a temporal sequence. In particular, a recurrent neural network can be interpreted as directed acyclic graph. In particular, the recurrent neural network can be a finite impulse recurrent neural network or an infinite impulse recurrent neural network (wherein a finite impulse network can be unrolled and replaced with a strictly feedforward neural network, and an infinite impulse network cannot be unrolled and replaced with a strictly feedforward neural network).

In particular, training a recurrent neural network can be based on the BPTT algorithm (acronym for "backpropagation through time"), on the RTRL algorithm (acronym for "real-time recurrent learning") and/or on genetic algorithms.

By using a recurrent machine learning model input data comprising sequences of variable length can be used. In particular, this implies that the method cannot be used only for a fixed number of input datasets (and needs to be trained differently for every other number of input datasets used as input), but can be used for an arbitrary number of input datasets. This implies that the whole set of training data, independent of the number of input datasets contained in different sequences, can be used within the training, and that training data is not reduced to training data corresponding to a certain number of successive input datasets.

Figure 6:
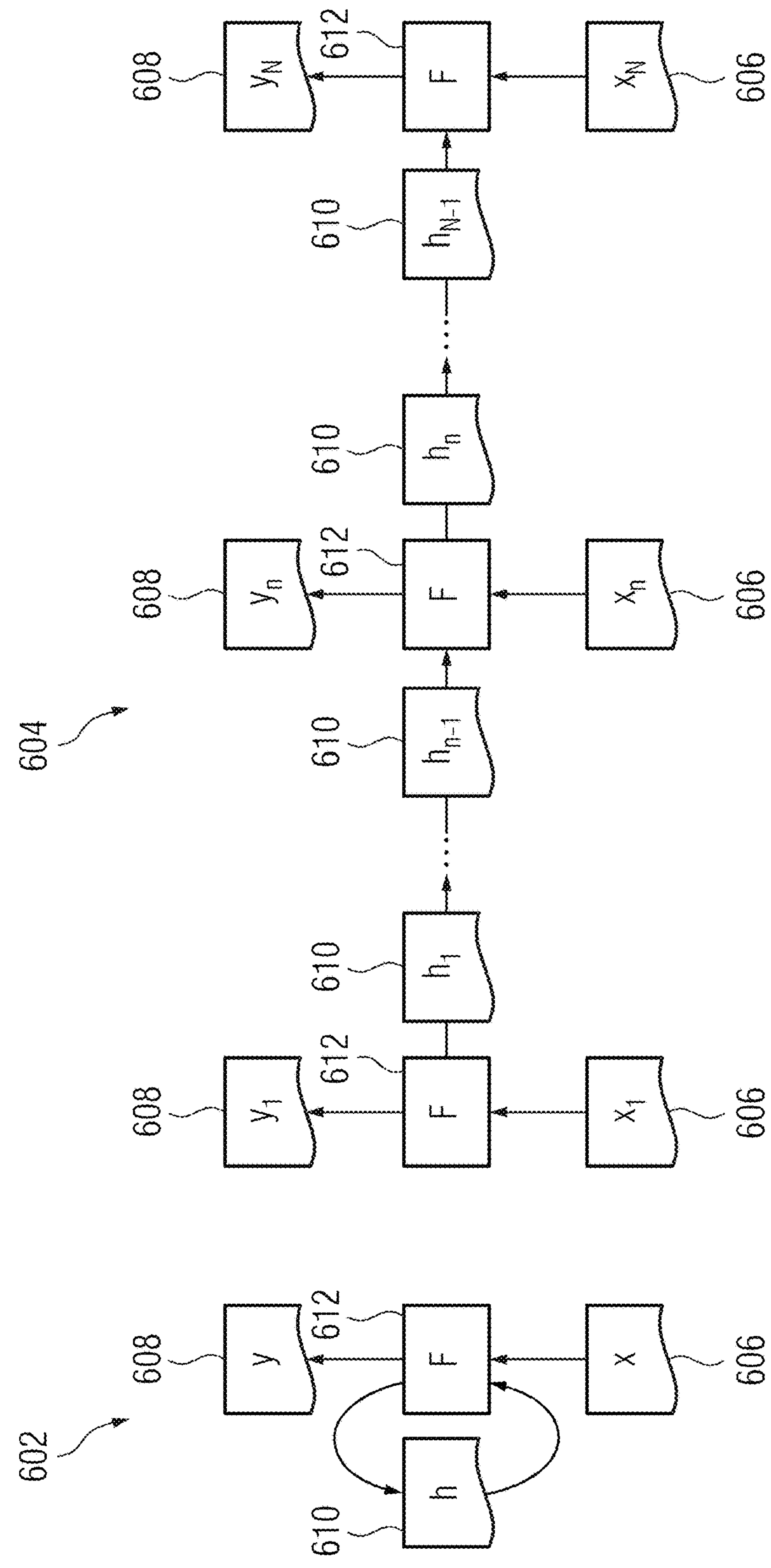
FIG. 6 shows a schematic structure of a recurrent machine learning model that may be used to implement one or more embodiments.

FIG. 6 shows the schematic structure of a recurrent machine learning model F, both in a recurrent representation 602 and in an unfolded representation 604, that may be used to implement one or more machine learning models described herein. The recurrent machine learning model takes as input several input datasets x, $x_1, \ldots, x_N$ 606 and creates a corresponding set of output datasets y, $y_1, \ldots, y_N$ 608. Furthermore, the output depends on a so-called hidden vector h, $h_1, \ldots, h_N$ 610, which implicitly comprises information about input datasets previously used as input for the recurrent machine learning model F 612. By using these hidden vectors h, $h_1, \ldots, h_N$ 610, a sequentiality of the input datasets can be leveraged.

In a single step of the processing, the recurrent machine learning model F 612 takes as input the hidden vector $h_{n-1}$ created within the previous step and an input dataset $x_n$. Within this step, the recurrent machine learning model F generates as output an updated hidden vector $h_n$ and an output dataset $y_n$. In other words, one step of processing calculates $(y_n, h_n)=F(x_n, h_{n-1})$, or by splitting the recurrent machine learning model F 612 into a part F(y) calculating the output data and F(h) calculating the hidden vector, one step of processing calculates $y_n=F^{(y)}(x_n, h_{n-1})$ and $h_n=F^{(h)}(x_n, h_{n-1})$. For the first processing step, $h_0$ can be chosen randomly or filled with all entries being zero. The parameters of the recurrent machine learning model F 612 that were trained based on training datasets before do not change between the different processing steps.

In particular, the output data and the hidden vector of a processing step depend on all the previous input datasets used in the previous steps. $y_n=F^{(y)}(x_n, F^{(h)}(x_{n-1}, h_{n-2}))$ and $h_n=F(h)(x_n, F^{(h)}(x_{n-1}, h_{n-2}))$.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatuses, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatuses, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 2. Certain steps or functions of the methods and workflows described herein, including one or more of the steps or functions of FIG. 1 or 2, may be performed by a server or by another processor in a network-based cloud-computing system. Certain steps or functions of the methods and workflows described herein, including one or more of the steps of FIG. 1 or 2, may be performed by a client computer in a network-based cloud computing system. The steps or functions of the methods and workflows described herein, including one or more of the steps of FIG. 1 or 2, may be performed by a server and/or by a client computer in a network-based cloud computing system, in any combination.

Systems, apparatuses, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

A high-level block diagram of an example computer 702 that may be used to implement systems, apparatuses, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method and workflow steps or functions of FIG. 1 or 2 can be defined by the computer program instructions stored in memory 710 and/or data storage device 712 and controlled by processor 704 executing the computer program instructions. For example, the computer program instructions can be implemented as computer executable code programmed by one skilled in the art to perform the method and workflow steps or functions of FIG. 1 or 2. Accordingly, by executing the computer program instructions, the processor 704 executes the method and workflow steps or functions of FIG. 1 or 2. Computer 702 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 708 may include a display device such as a cathode ray tube (CRT) or liquid crystal display (LCD) monitor for displaying information to the user, a keyboard, and a pointing device such as a mouse or a trackball by which the user can provide input to computer 702.

An image acquisition device 714 can be connected to the computer 702 to input image data (e.g., medical images) to the computer 702. It is possible to implement the image acquisition device 714 and the computer 702 as one device. It is also possible that the image acquisition device 714 and the computer 702 communicate wirelessly through a network. In a possible embodiment, the computer 702 can be located remotely with respect to the image acquisition device 714.

Any or all of the systems, apparatuses, and methods discussed herein may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The following is a list of non-limiting illustrative embodiments disclosed herein:

Illustrative embodiment 1. A computer-implemented method comprising: receiving 1) one or more input medical images of an anatomical object of a patient and 2) an input age associated with the patient; extracting a feature set from the one or more input medical images; encoding the extracted feature set with noise based on the input age associated with the patient using a machine learning based noise model; predicting an age associated with the patient based on the extracted feature set; denoising the encoded feature set based on the input age associated with the patient and the predicted age associated with the patient using a machine learning based denoising model; generating one or more synthetic images of the anatomical object of the patient based on the denoised feature set; and outputting the one or more synthetic images of the anatomical object of the patient.

Illustrative embodiment 2. The computer-implemented method according to illustrative embodiment 1, wherein denoising the encoded feature set based on the input age associated with the patient and the predicted age associated with the patient using a machine learning based denoising model comprises: denoising the encoded feature set based on a difference between the input age and the predicted age.

Illustrative embodiment 3. The computer-implemented method according to any one of illustrative embodiments 1-2, further comprising: predicting one or more abnormalities in the one or more input medical images based on the extracted feature set, wherein generating one or more synthetic images of the anatomical object of the patient based on the denoised feature set comprises generating the one or more synthetic images based on the one or more predicted abnormalities.

Illustrative embodiment 4. The computer-implemented method according to any one of illustrative embodiments 1-3, further comprising: generating an abnormality map by subtracting the one or more synthetic images from the one or more input medical images.

Illustrative embodiment 5. The computer-implemented method according to any one of illustrative embodiments 1-4, further comprising: determining a quantitative measure of difference in appearance based on the one or more synthetic images and the one or more input medical images.

Illustrative embodiment 6. The computer-implemented method according to any one of illustrative embodiments 1-5, further comprising: determining a predicted age difference as the difference between the input age and the predicted age.

Illustrative embodiment 7. The computer-implemented method according to any one of illustrative embodiments 1-6, wherein the machine learning based noise model and the machine learning based denoising model is the same latent diffusion model.

Illustrative embodiment 8. The computer-implemented method according to any one of illustrative embodiments 1-7, wherein the one or more synthetic images represent healthy-for-age images of the anatomical object for the input age.

Illustrative embodiment 9. The computer-implemented method according to any one of illustrative embodiments 1-8, wherein the anatomical object is a brain of the patient.

Illustrative embodiment 10. An apparatus comprising: means for receiving 1) one or more input medical images of an anatomical object of a patient and 2) an input age associated with the patient; means for extracting a feature set from the one or more input medical images; means for encoding the extracted feature set with noise based on the input age associated with the patient using a machine learning based noise model; means for predicting an age associated with the patient based on the extracted feature set; means for denoising the encoded feature set based on the input age associated with the patient and the predicted age associated with the patient using a machine learning based denoising model; means for generating one or more synthetic images of the anatomical object of the patient based on the denoised feature set; and means for outputting the one or more synthetic images of the anatomical object of the patient.

Illustrative embodiment 11. The apparatus according to illustrative embodiment 10, wherein the means for denoising the encoded feature set based on the input age associated with the patient and the predicted age associated with the patient using a machine learning based denoising model comprises: means for denoising the encoded feature set based on a difference between the input age and the predicted age.

Illustrative embodiment 12. The apparatus according to any one of illustrative embodiments 10-11, further comprising: means for predicting one or more abnormalities in the one or more input medical images based on the extracted feature set, wherein the means for generating one or more synthetic images of the anatomical object of the patient based on the denoised feature set comprises means for generating the one or more synthetic images based on the one or more predicted abnormalities.

Illustrative embodiment 13. The apparatus according to any one of illustrative embodiments 10-12, further comprising: means for generating an abnormality map by subtracting the one or more synthetic images from the one or more input medical images.

Illustrative embodiment 14. The apparatus according to any one of illustrative embodiments 10-13, further comprising: means for determining a quantitative measure of difference in appearance based on the one or more synthetic images and the one or more input medical images.

Illustrative embodiment 15. A non-transitory computer-readable storage medium comprising instructions which, when executed by a computer, cause the computer to carry out operations comprising: receiving 1) one or more input medical images of an anatomical object of a patient and 2) an input age associated with the patient; extracting a feature set from the one or more input medical images; encoding the extracted feature set with noise based on the input age associated with the patient using a machine learning based noise model; predicting an age associated with the patient based on the extracted feature set; denoising the encoded feature set based on the input age associated with the patient and the predicted age associated with the patient using a machine learning based denoising model; generating one or more synthetic images of the anatomical object of the patient based on the denoised feature set; and outputting the one or more synthetic images of the anatomical object of the patient.

Illustrative embodiment 16. The non-transitory computer-readable storage medium according to illustrative embodiment 15, wherein denoising the encoded feature set based on the input age associated with the patient and the predicted age associated with the patient using a machine learning based denoising model comprises: denoising the encoded feature set based on a difference between the input age and the predicted age.

Illustrative embodiment 17. The non-transitory computer-readable storage medium according to any one of illustrative embodiments 15-16, the operations further comprising: determining a predicted age difference as the difference between the input age and the predicted age.

Illustrative embodiment 18. The non-transitory computer-readable storage medium according to any one of illustrative embodiments 15-17, wherein the machine learning based noise model and the machine learning based denoising model is the same latent diffusion model.

Illustrative embodiment 19. The non-transitory computer-readable storage medium according to any one of illustrative embodiments 15-18, wherein the one or more synthetic images represent healthy-for-age images of the anatomical object for the input age.

Illustrative embodiment 20. The non-transitory computer-readable storage medium according to any one of illustrative embodiments 15-19, wherein the anatomical object is a brain of the patient.

The invention claimed is:

1. A computer-implemented method comprising:

receiving 1) one or more input medical images of an anatomical object of a patient and 2) an input age associated with the patient;

extracting a feature set from the one or more input medical images;

encoding the extracted feature set with noise based on the input age associated with the patient using a machine learning based noise model;

predicting an age associated with the patient based on the extracted feature set;

denoising the encoded feature set based on the input age associated with the patient and the predicted age associated with the patient using a machine learning based denoising model;

generating one or more synthetic images of the anatomical object of the patient based on the denoised feature set; and outputting the one or more synthetic images of the anatomical object of the patient.

2. The computer-implemented method of claim 1, wherein denoising the encoded feature set based on the input age associated with the patient and the predicted age associated with the patient using a machine learning based denoising model comprises:

denoising the encoded feature set based on a difference between the input age and the predicted age.

3. The computer-implemented method of claim 1, further comprising:

predicting one or more abnormalities in the one or more input medical images based on the extracted feature set, wherein generating one or more synthetic images of the anatomical object of the patient based on the denoised feature set comprises generating the one or more synthetic images based on the one or more predicted abnormalities.

4. The computer-implemented method of claim 1, further comprising:

generating an abnormality map by subtracting the one or more synthetic images from the one or more input medical images.

5. The computer-implemented method of claim 1, further comprising:

determining a quantitative measure of difference in appearance based on the one or more synthetic images and the one or more input medical images.

6. The computer-implemented method of claim 1, further comprising:

determining a predicted age difference as the difference between the input age and the predicted age.

7. The computer-implemented method of claim 1, wherein the machine learning based noise model and the machine learning based denoising model is the same latent diffusion model.

8. The computer-implemented method of claim 1, wherein the anatomical object is a brain of the patient.

9. An apparatus comprising:

means for receiving 1) one or more input medical images of an anatomical object of a patient and 2) an input age associated with the patient;

means for extracting a feature set from the one or more input medical images;

means for encoding the extracted feature set with noise based on the input age associated with the patient using a machine learning based noise model;

means for predicting an age associated with the patient based on the extracted feature set;

means for denoising the encoded feature set based on the input age associated with the patient and the predicted age associated with the patient using a machine learning based denoising model;

means for generating one or more synthetic images of the anatomical object of the patient based on the denoised feature set; and means for outputting the one or more synthetic images of the anatomical object of the patient.

10. The apparatus of claim 9, wherein the means for denoising the encoded feature set based on the input age associated with the patient and the predicted age associated with the patient using a machine learning based denoising model comprises:

means for denoising the encoded feature set based on a difference between the input age and the predicted age.

11. The apparatus of claim 9, further comprising:

means for predicting one or more abnormalities in the one or more input medical images based on the extracted feature set, wherein the means for generating one or more synthetic images of the anatomical object of the patient based on the denoised feature set comprises means for generating the one or more synthetic images based on the one or more predicted abnormalities.

12. The apparatus of claim 9, further comprising:

means for generating an abnormality map by subtracting the one or more synthetic images from the one or more input medical images.

13. The apparatus of claim 9, further comprising:

means for determining a quantitative measure of difference in appearance based on the one or more synthetic images and the one or more input medical images.

14. A non-transitory computer-readable storage medium comprising instructions which, when executed by a computer, cause the computer to carry out operations comprising:

receiving 1) one or more input medical images of an anatomical object of a patient and 2) an input age associated with the patient;

extracting a feature set from the one or more input medical images;

encoding the extracted feature set with noise based on the input age associated with the patient using a machine learning based noise model;

predicting an age associated with the patient based on the extracted feature set;

denoising the encoded feature set based on the input age associated with the patient and the predicted age associated with the patient using a machine learning based denoising model;

generating one or more synthetic images of the anatomical object of the patient based on the denoised feature set; and outputting the one or more synthetic images of the anatomical object of the patient.

15. The non-transitory computer-readable storage medium of claim 14, wherein denoising the encoded feature set based on the input age associated with the patient and the predicted age associated with the patient using a machine learning based denoising model comprises:

denoising the encoded feature set based on a difference between the input age and the predicted age.

16. The non-transitory computer-readable storage medium of claim 14, the operations further comprising:

determining a predicted age difference as the difference between the input age and the predicted age.

17. The non-transitory computer-readable storage medium of claim 14, wherein the machine learning based noise model and the machine learning based denoising model is the same latent diffusion model.

18. The non-transitory computer-readable storage medium of claim 14, wherein the anatomical object is a brain of the patient.

19. The computer-implemented method of claim 1, further comprising:

comparing the one or more synthetic images to the one or more input medical images to detect abnormal aging progression.

20. The non-transitory computer-readable storage medium of claim 14, the operations further comprising:

comparing the one or more synthetic images to the one or more input medical images to detect abnormal aging progression.

* * * * *